United States Patent [19]

Bjorkholm

[11] Patent Number: 4,511,799
[45] Date of Patent: Apr. 16, 1985

[54] DUAL ENERGY IMAGING

[75] Inventor: Paul J. Bjorkholm, Sharon, Mass.

[73] Assignee: American Science and Engineering, Inc., Cambridge, Mass.

[21] Appl. No.: 448,461

[22] Filed: Dec. 10, 1982

[51] Int. Cl.³ .................. G01T 1/16; G01T 1/185; G01T 1/20
[52] U.S. Cl. .................. 250/367; 250/370; 250/374
[58] Field of Search .............. 250/367, 370 E, 370 I, 250/366, 363 R, 358.1, 375, 374, 385; 378/5

[56] References Cited

U.S. PATENT DOCUMENTS

| 2,445,305 | 7/1948 | Hochgesang | 250/266 |
|---|---|---|---|
| 3,582,651 | 6/1971 | Siedband | 378/99 |
| 3,790,799 | 2/1974 | Stein et al. | 378/146 |
| 3,848,130 | 11/1974 | Macovski | 250/369 |
| 3,854,049 | 12/1974 | Mistretta et al. | 378/62 |
| 3,894,181 | 7/1975 | Mistretta | 358/93 |
| 3,965,358 | 6/1976 | Macovski | 250/369 |
| 3,974,386 | 8/1976 | Mistretta et al. | 378/99 |
| 4,029,963 | 6/1977 | Alvarez et al. | 250/360 |
| 4,031,401 | 6/1977 | Jacob | 378/146 |
| 4,204,225 | 5/1980 | Mistretta | 128/695 |
| 4,204,226 | 5/1980 | Mistretta et al. | 358/111 |
| 4,242,583 | 12/1980 | Annis et al. | 378/146 |
| 4,247,774 | 1/1981 | Brooks | 250/367 |
| 4,260,898 | 4/1981 | Annis | 378/146 |
| 4,317,037 | 2/1982 | Suzuki et al. | 250/367 |
| 4,413,353 | 11/1983 | Macovski et al. | 378/62 |

FOREIGN PATENT DOCUMENTS 52-2777  1/1977  Japan .................. 250/370 E

Primary Examiner—Janice A. Howell
Assistant Examiner—Constantine Hannaher
Attorney, Agent, or Firm—Pollock, Vande Sande and Priddy

[57] ABSTRACT

Dual energy imaging develops simultaneous signals from transmitted energy of different characteristics. The detector includes two serially arranged detectors. A first detector preferentially absorbs lower level radiant energy and the second detector preferentially absorbs higher radiant energy. The detectors may be identical in which case the preferential characteristic is developed by reason of the detector's position. Alternatively, the characteristics of the detectors may be selected to produce the desired effect, e.g. a gaseous detector may be pressurized in accordance with its function, a scintillating screen may be tilted or its length may be selected to produce the desired absorption characteristic.

8 Claims, 7 Drawing Figures

DUAL ENERGY IMAGING

DESCRIPTION

1. Field of the Invention

The invention relates to improvements in imaging using penetrating radiant energy, for example x-rays.

2. Background Art

Mistretta and Brody have made improvements in what is here termed dual energy imaging. These improvements allow illumination of a complex object (one including two or more different substances such as different elements, compounds or tissues) to allow a selective display related to some but not all of the different components of the object. This is a very significant improvement in the field of imaging, since in the real world most objects which are imaged are complex objects, and many problems arise because the display is cluttered with the inclusion of images of irrelevant components. Aside from merely cluttering the display, irrelevant images may actually hide or obscure desired images. It is thus a prime object of the invention to improve dual energy imaging.

Two of the problems evidenced in the prior art dual energy imaging techniques relate to the type of illumination employed and the lack of simultaneity in the data collected.

The dual energy imaging techniques known to the prior art all require control of the illumination energy. In one of the techniques (Mistretta), three different exposures are made using illumination of three different energies, each of which are monochromatic or nearly so. Typically, nearly monochromatic illumination is obtained by filtering energy from an uncontrolled source. This filtering obviously reduces the incident illumination on the object and has the concomitant disadvantage that the resulting image is photon limited.

While Brody's work is less severely limited, i.e. he uses two illuminations, each with a relatively broader band of illumination energies; the two illuminations are still filtered to the extent that the illumination energies do not "overlap too much". While the results of Brody's work are not as photon limited as Mistretta's, the filtering necessary to obtain the desired characteristics in the illumination energy still reduces the illumination intensity.

A further disadvantage, which is common to all the prior art work in this field is that the different exposures employed are time sequential, i.e. the data collected during the several exposures lack simultaneity. Obviously, images taken at different times will only be identical if motion is absent, and many interesting subjects are inherently subject to motion.

It is therefore one object of the present invention to provide a method and apparatus for dual energy imaging which collects data simultaneously thus eliminating motion artifacts in the images. It is another object of the present invention to provide a method and apparatus for dual energy imaging which does not require filtering or processing of the illumination energy and is not subject to being photon limited, as is the prior art.

SUMMARY OF THE INVENTION

These and other objects of the invention are met by providing an imaging apparatus including a source of penetrating radiant energy, means for directing the penetrating radiant energy emitted by the source so as to travel a path toward a target area, detector means located beyond the target area along the path of said radiant energy for producing signals representative of radiant energy reaching the detector means. The invention is characterized in that the detector means includes at least a first energy detector for converting radiant energy of a first characteristic to a first signal and a second energy detector for converting radiant energy of a second characteristic, different from the first characteristic, to a second signal. As is described hereinafter, in accordance with preferred embodiments of the invention, the sensitivity of the first energy detector falls off at a relatively lower level energy as compared with the sensitivity of the second energy detector which is responsive to radiant energy of a relatively higher energy level.

For shorthand purposes, the first energy detector of the preferred embodiments can be called a 'thin' detector and the second energy detector can be called a 'thick' detector. The adjective 'thin' implies an increasing inability to absorb harder and harder radiant energy, i.e. it is most sensitive to low energy radiant energy. The 'thick' adjective implies that the detector characteristic falls off at a higher energy level than the characteristic of the 'thin' detector. However as will be explained, the detectors may have the identical characteristic. In some cases the order of the thin and thick detectors may be reversed.

Detector means as is recited above include first and second energy detectors located with the first energy detector in front of the second energy detector along the path of travel of the radiant energy. In the preferred embodiments, the first energy detector has increased sensitivity to and therefore preferentially absorbs lower level radiant energy, and thus higher level radiant energy passes through the first energy detector and is incident on the second energy detector. The second energy detector may be arranged to respond to illumination of a higher energy level than the first energy detector.

Preferred embodiments of the invention described hereinafter may employ either gaseous, liquid or solid state radiant energy detectors. In the case of a gaseous energy detector, the different energy responsive characteristics may be provided by pressurizing the gas in the first energy detector at a relatively lower pressure than the gas in the second energy detector.

In the case of solid state radiant energy detectors, a single continuous scintillating material is common to one form of the first and second energy detectors. The first energy detector includes a portion of the scintillating crystal located nearer the source of illumination than the portion of the scintillating crystal associated with the second energy detector. The first and second energy detectors further include opto-electronic transducers located adjacent respective portions of the scintillating crystal so that the opto-electronic transducer (or diode) forming part of the first energy detector is responsive to light energy emitted by that portion of the scintillating crystal associated with the first energy detector and correspondingly the opto-electronic transducer (or diode) associated with the second energy detector is located adjacent that portion of the scintillating crystal which is associated with the second energy detector.

In other embodiments of the invention, first and/or second energy detectors may comprise a scintillating screen. The energy responsive characteristics of the screen responsive can be varied by merely varying the angle a normal to the screen makes with the path of the radiant energy. By increasing the angle (from zero) the effective "length" of the screen is increased making it responsive to penetrating radiant energy of higher and higher energy levels.

The first and second signals produced by the first and second detectors can then be processed, stored and displayed in accordance with conventional dual energy imaging. Furthermore, the dual energy imaging described in my co-pending application, incorporated herein by this reference, entitled "Improvements in Imaging", filed Sept. 29, 1982 and assigned to the assignee of this application, may be used.

The 'thin' and 'thick' characteristics of the detectors can be obtained by tailoring the device or by its relative positioning.

In special cases, the 'thick' detector may precede the 'thin' detector, but in this case the device characteristics must be tailored as will be described below.

The dual energy imaging in accordance with the invention can be achieved using conventional flying spot scanning illumination. With flying spot illumination each of the detectors can be a line detector. However, the invention is also applicable to fan beam illumination. In this case, each of the detectors consists of a series of 'point' detectors. Finally the invention is applicable to area illumination. In this last case each of the detectors consists of a matrix of 'point' detectors.

While an X-ray illumination source is described, other types of radiant energy can be used with appropriate detectors.

BRIEF DESCRIPTION OF THE DRAWINGS

The present invention will now be further described in the following portions of the specification when taken in conjunction with the attached drawings in which like reference characters identify identical apparatus and in which.

DETAILED DESCRIPTION OF PREFERRED EMBODIMENTS

Figure 1:
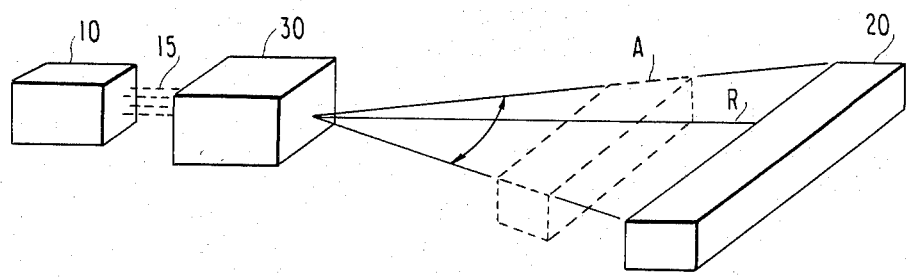
FIG. 1 is a schematic diagram of the apparatus of the invention.

As shown in FIG. 1, the apparatus of the invention includes, in the main, three components. A source of penetrating radiant energy 10 in one component. The penetrating radiant energy 15 emitted by the source 10 (for example, such as an x-ray tube) impinges on apparatus 30 to direct the radiant energy toward the target area A. In addition to directing (perhaps collimating) the energy emitted by the source 10, the apparatus 30 may also form a flying spot beam, for repeatedly scanning a line in space. Since the apparatus for shaping the penetrating radiant energy 15 emitted by the source 10, and in those cases in which a flying spot beam is desired, for forming such a spot beam, is well known to those skilled in the art, the apparatus 30 need not be further described herein. Reference is made to U.S. Pat. Nos. 4,031,401; RE 2,544; 3,790,799; 4,242,583 and 4,260,898.

Assuming that the apparatus 30 forms a flying spot beam, then as shown in FIG. 1 the penetrating radiant energy at any instant takes the form of a ray R, which, as a function of time, sweeps repeatedly back and forth in the region illustrated in the drawing. A target to be illuminated is located in the target area A, and finally the radiant energy transmitted through the object in the target area A impinges on detector means 20.

Figure 2:
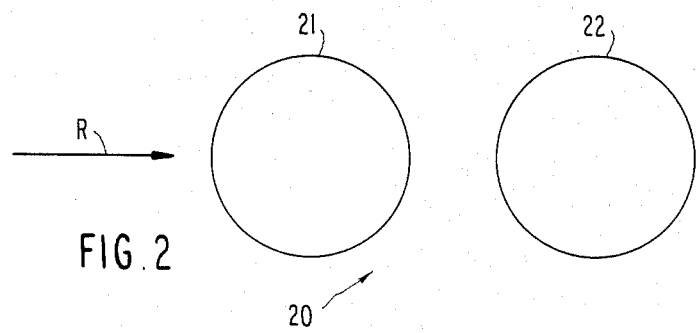
FIGS. 2, 4, 5 and 6 are schematic showing different types of detector means 20.
Figure 4:
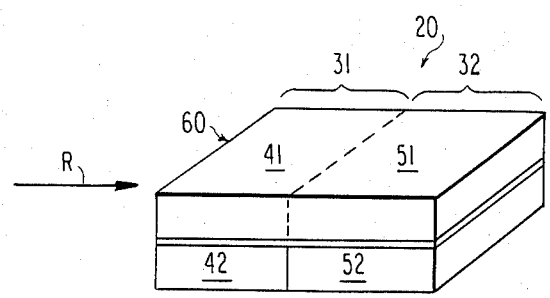
Figure 5:
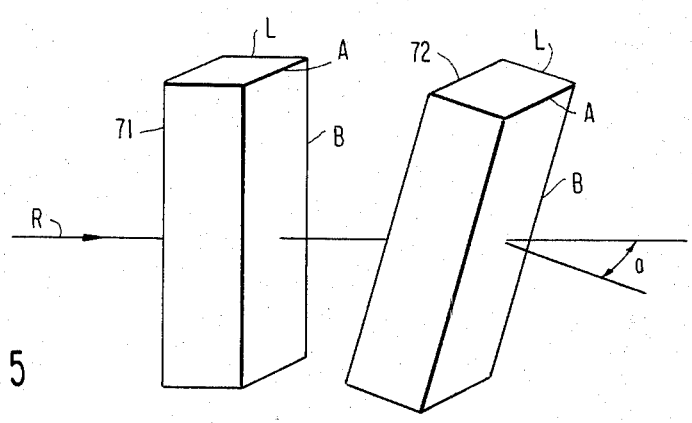

For purposes of developing the dual energy imaging, the detector means 20 can take a variety of forms, three different embodiments of which are illustrated respectively in FIGS. 2, 4 and 5.

Figure 3:
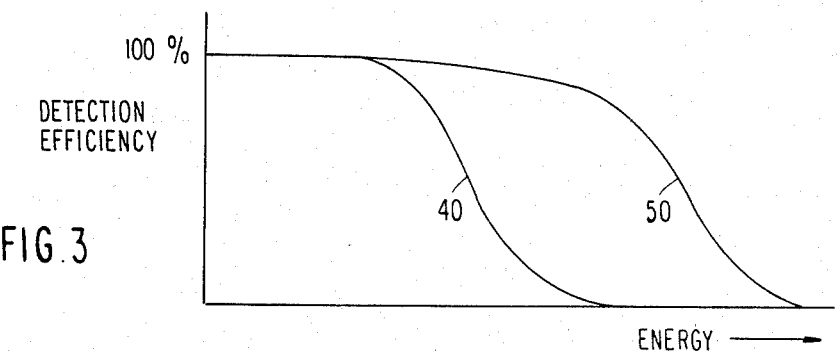
FIGS. 3 and 7 are plots of detection efficiency versus energy level for the different embodiments of the detector means 20.

Referring now to FIG. 2, the typical ray R is shown impinging on the detector means 20 which, in the embodiment of FIG. 2 includes a first energy detector 21 and a second energy detector 22. As seen in FIG. 2, the first and second energy detectors 21 and 22 (shown in cross-section in FIG. 2) are located serially in the path R taken by the penetrating radiant energy so that penetrating radiant energy intercepts the first energy detector 21 and energy passing through the first energy detector 21 impinges on the second energy detector 22. In the embodiment illustrated in FIG. 2, the first and second energy detectors each may comprise a gaseous detector associated with a transducer to convert energy from absorbed X-rays (or other radiant energy such as gamma rays) to electrical signals. In accordance with the invention, as will be described hereinafter, the first energy detector 21 is responsive to radiant energy of a first characteristic, and the second energy detector 22 is responsive to radiant energy of a second characteristic different from the first characteristic. In particular, the first energy detector 21 has a sensitivity characteristic which falls off at radiant energy of lower energy level than the characteristic of energy detector 22. Referring briefly to FIG. 3 which is a plot of detection efficiency versus incident energy for the first and second energy detectors, the curve 40 identifies the characteristic of the first energy detector 21 and the curve 50 identifies the characteristic of the second energy detector 22.

Returning briefly to FIG. 2, the energy detectors 21 and 22 can comprise gas filled tubes, filled with an identical gas, with the energy detector 22 pressurized to a pressure greater than that of the energy detector 21. Under these circumstances, the detection of efficiency of the first energy detector 21 drops off as the incident energy increases in energy level. While the second energy detector 22 illustrates the same characteristic (of falling efficiency as energy increases) because of the increased gas pressure in energy detector 22, the fall off in efficiency in the second energy detector occurs at a higher energy level than in the first. As a result, the second energy detector 22 has increased sensitivity to energy of a level higher than the energy to which energy detector 21 is responsive to. This result is also contributed to by the relative location of the two detectors, one in front of the other. Since the absorption of radiant energy is proportional to the incident flux, the detector 21, in absorbing lower energy radiant energy, reduces the lower energy radiant energy reaching detector 22. This reduces the apparent sensitivity of detector 22 to lower level radiant energy.

FIG. 4 illustrates another embodiment of the detector means 20, and in contrast to FIG. 2 wherein the detector means 20 includes two individual energy detectors 21 and 22, the detector means 20 of FIG. 4 includes a single scintillating material such as crystal 60. Associated with the single scintillating crystal 60 is a pair of opto-electronic transducers or diodes 42 and 52. The diode 42 is associated with a portion 41 of the scintillating crystal 60, and the diode 52 is associated with a different portion 51 of the scintillating crystal 60. As shown in FIG. 4, the portion 41 of the scintillating crystal 60 is located closer to the target area A than is the portion 51, in the direction of travel of the radiant energy R. Accordingly, the detector means of FIG. 4 includes a first energy detector 31 and a second energy detector 32. Each of the energy detectors 31 and 32 includes its respective diode (42 or 52) and a portion of the scintillating crystal 41 or 51. It should be understood by those skilled in the art that the division of the crystal 60 (the dotted line) shown in FIG. 4 is theoretical; in practice there need be no physical division between portions 41 and 51 of the scintillating crystal 60. Because of the location of the diodes 42 and 52, however, each diode is responsive to optical energy emitted by one portion or the other (41 or 51) of the scintillating crystal 60. By selecting the scintillating material 60 and the length (in the direction of the ray R) of the portions 41 and 51, we can assure that a given (high) percentage of the energy below a selected energy $E_1$ is absorbed in portion 41 and a given (high) percentage of the energy below a selected, higher, energy $E_2$ ($E_2 > E_1$) is absorbed in portion 51. In this fashion, the optical emissions of the portion 41 and 51 are related to different energy levels. Those skilled in the art will appreciate that the scintillating material may be uniform and that the foregoing characteristic follows from the fact that the energy flux absorbed over any small incremental distance of the scintillating material is proportional to the incident flux. Thus, lower energy is preferentially absorbed over portion 41 and portion 51 sees a higher proportion of the higher energy level. This effect requires little or no light migration along the energy path, R. This is easily arranged in conventional fashion. This preferential absorption can be accentuated as shown in FIG. 6.

Figure 6:
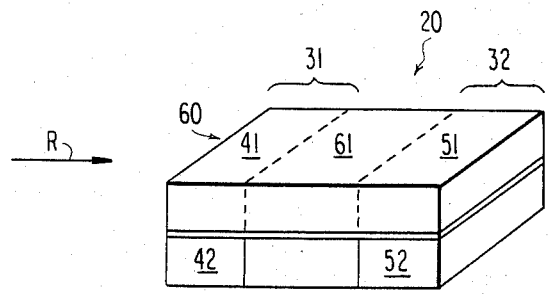

FIG. 6 is identical to FIG. 4 except that the material 60 is now composed of three portions, 41, 51 and 61, with portion 61 located between 41 and 51. Since the diodes 42 and 52 remain adjacent portions 41 and 51, respectively, the energy absorbed in portion 61 increases the preferential absorption of portion 51 to higher level radiant energy. Note that with either embodiments of FIG. 4 or 6 the preferential absorption may be achieved merely by preferential location since in other respects the detectors 31 and 32 are identical. The use of detectors with identical characteristics is of course not confined to the solid state detectors shown in FIGS. 4 and 6.

Finally, in still another embodiment of the invention, shown in FIG. 5, the first and second energy detectors comprise first and second scintillating screens 71 and 72, respectively. The manufacture of scintillating screens are well known to those skilled in the art and therefore a specific description of the parameters of the screen 71 and 72 is not necessary. However, those skilled in the art are aware that the stopping power of a scintillating screen depends on the length of the screen in the direction of travel of the radiant energy. Screens of identical dimensions can be arranged to have different energy responsive characteristics, by selecting the angle the screen makes with the direction of the radiant energy.

More particularly, it may be desired to have the first energy detector with sensitivity limited to lower level radiant energy, and the second energy detector with a higher sensitivity to higher level radiant energy. Screens of identical dimensions can be located to achieve these goals by arranging the second screen so that a normal to the screen makes a greater angle to the direction of the radiant energy R, than the angle a normal to the first screen makes with the same direction. Typically, a normal to the first screen will be parallel to the direction R, so the desired effect can be produced by tilting the second screen. By reason of this angular orientation, the "length" of the screen seen by the radiant energy is greater for the second screen than for the first. This increased length increases the sensitivity of the second screen to higher energy levels as compared to the sensitivity of the first screen.

Thus, FIG. 5 shows two identical screens 71 and 72, each of length L, in the direction of the ray R, with other dimensions A and B, respectively. Since screen 72 is "tilted" with respect to the direction R by the angle a, the length of screen 72 seen by the radiant energy is $L/\cos a$. Since a is by definition $\neq 0$, $L/\cos a > L$.

Of course, if desired, the two scintillating screens 71 and 72 could be arranged to make a common angle with the direction of radiant energy R, wherein the characteristics (dimensions, material, etc.) of this second screen are varied with respect to the first so as to increase the "length" or stopping power of the second screen in the direction of the radiant energy R, as compared to the "length" or stopping power of the first screen.

Finally, the preferential absorption can be solely a result of preferential location, i.e. the two screens 71 and 72 may be identical in size and angle.

In the several embodiments of the invention described with reference to FIGS. 2, 4 and 5, the description has been in terms of a pair of gaseous radiant energy detectors, a pair of scintillating crystal radiant energy detectors or a pair of scintillating screen radiant energy detectors. These embodiments of the invention have been described for convenience, and those skilled in the art will be aware that there is no requirement that the first and second energy detectors be of the same type, i.e. gaseous and solid state energy detectors can be used together. What is essential is that the first energy detector has a particular sensitivity characteristic, that it allows some flux to pass therethrough, and that the second energy detector be sensitive to the flux emitted by the first energy detector. In practice, this almost always requires that the two detectors be serially arranged with the first (or thin) energy detector located "in front" of the second (or thick) energy detector.

The preceding discussion, given in terms of a flying spot scanner, requires only two detectors, a raster image being produced by the motion of the flying spot and the (slower) indexing of the target perpendicular to the plane described by the flying spot (if necessary). However, the art also uses a line of detectors (usually in conjunction with a fan beam), made up of a linear array of detector cells as well as an area detector (used in conjunction with a beam having a cross-section of similar form) made up of a two dimensional array of detector cells. Those skilled in the art will readily perceive that the invention can be applied to linear detector arrays as well as two dimensional detector arrays. In either case a second detector, identical to the first, is located in the radiant energy beam path.

The specific embodiments of the invention described here consisted of two energy detectors. However, the invention can be applied to more than two energy detectors. For example, in FIG. 6 there may be added one or more additional photo-diode(s) adjacent the region 61.

While the usual case includes the detectors in a serial arrangement with the lower energy (or 'thin') detector leading the higher energy (or 'thick') detector, that is also not essential. A high energy (or 'thick') detector can lead the lower energy (or 'thin') detector so long as the 'thick' detector passes sufficient lower energy radiant energy to be detected by the 'thin' detector.

For example, this can be achieved by using the edge transition in the stopping material of the first detector. The first detector is chosen so its characteristic has an absorption edge at an energy just below the lowest energy of diagnostic interest. At greater energies the absorption increases leaving a low energy "window" which can be detected by the second energy detector. The second energy detector has an absorption edge at a different energy than the edge of the material of the first energy detector.

Figure 7:
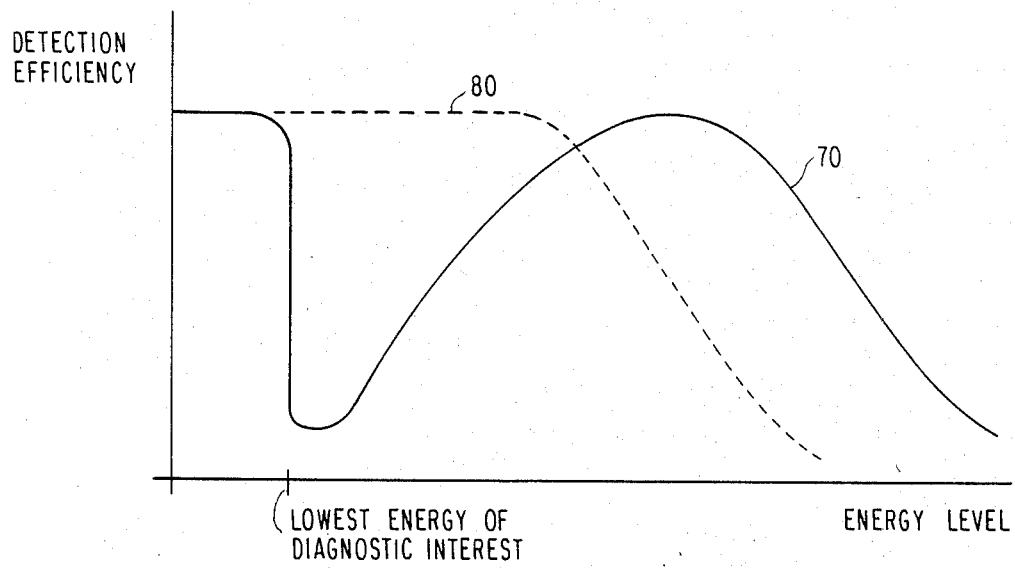

For example, the detector combination of any of FIGS. 2, 4, 5 or 6 is used. The first or 'thick' detector has a sensitivity characteristic 70 (see FIG. 7), the second or 'thin' detector has the sensitivity characteristic 80.

Those skilled in the art will realize that a characteristic like the characteristic 70 is available from many materials, the particular detector will be chosen based on the composition of the object being imaged. For example, tungsten has an edge at 69.5 kv and any iodinated scintillator has an edge at 33 kv.

It should be apparent from the foregoing that the signals produced by the two detectors can be processed and displayed to produce the advantages of dual energy imaging. In contrast to the prior art, the images are simultaneously obtained, thus eliminating motion artifacts. Furthermore, there are no artificial constraints on the illumination such that photon limiting is not expected.

I claim:

1. Apparatus for selectively imaging as a function of radiant energy levels, said apparatus comprising:
   a source of penetrating radiant energy,
   means for directing said radiant energy toward a target area,
   radiant energy detecting means located in a path of said radiant energy and including:
   a first scintillating screen detecting means with a surface having a normal at a first angle to said path of radiant energy for producing first signals corresponding to incident radiant energy, and
   a second scintillating screen detecting means, located in said path but beyond said first scintillating screen detecting means, with a surface having a normal at a second angle to said path of radiant energy for producing second signals corresponding to incident radiant energy, said second angle greater than said first angle.

2. Apparatus for selectively imaging as a function of radiant energy levels, said apparatus comprising:
   a source of penetrating radiant energy, means for directing said radiant energy toward a target area,
   radiant energy detecting means, comprising a single scintillating crystal, located in a path of said radiant energy and including:
   first detecting means for producing first signals corresponding to incident radiant energy, said first detecting means including a dedicated transducer and a portion of said single scintillating crystal and
   second detecting means, located in said path of travel of said radiant energy but beyond said first detecting means for producing second signals corresponding to radiant energy incident on said second detecting means, said second detecting means including a dedicated transducer and another portion of said single scintillating crystal.

3. The device of claim 2 in which each of said portions are directly adjacent.

4. The device of claim 2 in which said portions are separated.

5. Apparatus useful in imaging comprising:
   a source of penetrating radiant energy,
   means for directing penetrating radiant energy emitted by said source to travel a path toward a target area,
   detector means located beyond said target area along the path of said radiant energy for producing signals representative of radiant energy reaching said detector means, said detector means including:
   first energy detector means for converting radiant energy to a first signal, said first energy detector means having a first detection efficiency as a function of radiant energy, and
   second energy detector means located in said path but beyond said first energy detector means, for converting radiant energy to a second signal, said second energy detector means having a second detection efficiency, as a function of radiant energy, different from said first detection efficiency,
   wherein said first detection efficiency has a lower sensitivity to radiant energy in a first energy range and said second detection efficiency has a lower sensitivity to radiant energy in a second, higher, energy range.

6. The device of claim 5 in which said first and second energy detectors are each gas filled detectors.

7. The device of claim 5 in which said first and second energy detectors are each scintillating screens.

8. The device of claim 5 in which said first and second energy detectors comprise a scintillating crystal.

* * * * *